United States Patent [19]
Nyhus

[11] Patent Number: 6,121,525
[45] Date of Patent: Sep. 19, 2000

[54] INBRED CORN LINE ZS4199

[75] Inventor: Kris Nyhus, New Ulm, Minn.

[73] Assignee: Advanta Technology Limited, Lincolnshire, United Kingdom

[21] Appl. No.: 09/270,878

[22] Filed: Mar. 17, 1999

[51] Int. Cl.[7] .............................. A01H 5/00; A01H 5/10; A01H 1/04; A01H 4/00; C12N 5/04

[52] U.S. Cl. ................... 800/320.1; 800/275; 800/300.1; 800/301; 800/302; 435/412; 435/424; 435/430; 435/430.1

[58] Field of Search ................................. 800/320.1, 275, 800/298, 271, 300.1, 265, 301, 302; 435/412, 424, 430, 430.1

[56] References Cited

PUBLICATIONS

Phillips et al. "Cell/Tissue Culture and In Vitro Manipulation", In Corn and Corn Improvement, 3rd Ed., ASA Publication, #18, pp. 345–349 & 356–357, 1988.
Conger, B.V., F.J. Novak, R. Afra, and K. Erdelsky. "Somatic embryogenesis from cultured leaf segments of *Zea mays*", Plant Cell Reports, 6:345–347 (1987).
Duncan, D.R., M.E. Williams, B.E. Zehr and J.M. Widholm. "The production of callus capable of plant regeneration from immature embryos of numerous *Zea mays* genotypes", Planta, 165:322–332 (1985).
Edallo, et al., "Chromosomal Variation and Frequency of Spontaneous Mutation Associated with in Vitro Culture and Plant Regeneration in Maize" Maydica XXVI, pp. 39–56 (1981).
Forsberg, R.A. and R.R. Smith. "Sources, Maintenance, and Utilization of Parental Material", Hybridization of Crop Plants, Chapter 4, pp. 65–81 (1980).
Green, C.E. and R.L. Phillips. "Plant Regeneration from Tissue Cultures of Maize", Crop Science, vol. 15, pp. 417–421 (1975).
Green, C.E. and C.A. Rhodes. "Plant Regeneration in Tissue Cultures of Maize", Maize for Biological Research, pp. 367–372 (1982).
Hallauer, et al, "Corn Breeding", Corn and Corn Improvement pp. 463–564 (1988). Sprague et al, eds.
Lowe, Keith. European Patent Application 0 160 390. (1985).
Meghji, M.R., J.W. Dudley, R.J. Lambert, and G.F. Sprague. "Inbreeding Depression, Inbred and Hybrid Grain Yields, and Other Traits of Maize Genotypes Representing Three Eras". Crop Science, vol. 24, pp. 545–549 (1984).
Phillips, et al., "Cell/Tissue Culture and In Vitro Manipulation", In Corn & Corn Improvement, 3rd Ed., ASA Publication, #18, pp. 345–349 & 356–357 (1988).
Poehlman, John Milton. *Breeding Field Crop*, AVI Publishing Company, Inc., Westport, Connecticut, pp. 237–246 (1987).
Sass (1977) "Morphology". In Corn & Corn Improvement. ASA Publication. Madison, WI, pp. 89–109.
Songstad, David D., David R. Duncan, and Jack M. Widholm. "Effect of 1–aminocyclopropane–1–carboxylic acid, silver nitrate, and norbornadiene on plant regeneration from maize callus cultures", Plant Cell Reports, 7:262–265 (1988).
Tomes, et al, "the Effect of Parental Genotype on Initiation of Embryogenic callus from Elite Maize (*Zea mays*l.) Germplasm". Theor. Appl. Genet. 70., pp. 505–509. (1985).
Troyer, et al., "Selection for Early Flowering in Corn: 10 Late Synthesis". Crop Science, vol. 25, pp. 695–697 (1985).
Umbeck, et al. "Reversion of Male–Sterile T–Cytoplasm Maize to Male Fertility in Tissue Culture", Crop Science vol. 23, pp. 584–588 (1983).
Wright, H., "Commercial Hybrid Seed Production", Hybridization of Crop Plants, pp. 161–176, (1980).
Wych, R.D., "Production of Hybrid Seed Corn"; Corn and Corn Improvement, pp. 565–607 (1988).

*Primary Examiner*—Gary Benzion
*Assistant Examiner*—Melissa L. Kimball
*Attorney, Agent, or Firm*—Dana Rewoldt

[57] ABSTRACT

Broadly this invention provides inbred corn line ZS4199. The methods for producing a corn plant by crossing the inbred line ZS4199 are encompassed by the invention. Additionally, the invention relates to the various parts of inbred ZS4199 including culturable cells. This invention relates to a hybrid corn seeds and plants produced by crossing the inbred line ZS4199 with at least one other corn line. This invention also relates to hybrid corn seeds and plants produced by crossing the isogenic inbred line ZS4199 containing at least one mutant gene or a transgene with at least one other corn line.

17 Claims, No Drawings

INBRED CORN LINE ZS4199

FIELD OF THE INVENTION

This invention is in the field of corn breeding, specifically relating to an inbred corn line designated ZS4199.

BACKGROUND OF THE INVENTION

The original maize plant was indigenous to the Western Hemisphere. The plants were weedlike and only through the efforts of early breeders were a cultivated crop species developed. The crop cultivated by early breeders, like the crop today, would be wind pollinated. The physical traits of maize are such that self-pollination or cross-pollination between plants can occur. Each plant has a separate male and female flower, the tassel and ear, respectively. Natural pollination occurs when wind transfers pollen from tassel to the silks on the corn ears. This type of pollination contributed to the wide variation of maize varieties present in the Western Hemisphere.

The development of a planned breeding program for maize only occurred in the last century. A large part of the development of the maize product in to a profitable agricultural crop was due to the work done by land grant colleges. Originally, maize was an open pollinated variety having heterogeneous genotypes. The maize farmer selected uniform ears from the yield of these genotypes and reserved them for planting the next season. The result was a field of maize plants that were segregating for a variety of traits. This type of maize selection led to at most incremental increases in seed yield.

Large increases in seed yield were the result of the development of hybrid corn varieties in planned breeding programs. Hybrids were developed by selecting corn lines and selfing these lines for several generations to develop homozygous pure inbred lines and crossing selected inbred lines with other inbred lines to produce hybrid progeny (F1). Although hybrids are robust and vigorous plants due to heterosis, inbred lines are less vigorous and can be difficult to produce since the inbreeding process in corn decreases the vigor. However, when two inbred lines are crossed, the hybrid plant evidences greatly increases vigor compared to open pollinated segregating maize plants. An important factor of the homozygosity and the homogeneity of the inbred lines is that the hybrid from any cross will be the same, and can be reproduced.

The ultimate objected of the commercial maize seed companies is to produce high yielding, agronomically sound plants, which perform well in certain regions or areas of the Corn Belt. To produce these types of hybrids, the companies must develop inbreds that carry needed traits into the hybrid combination. Hybrids are not often uniformly adapted for the entire Corn Belt, but most often are specifically adapted for regions of the Corn Belt. Northern regions of the Corn Belt require shorter season hybrids than do southern regions of the Corn Belt. Hybrids that grow well in Colorado and Nebraska soils may not flourish in richer Illinois and Iowa soil. Thus, a variety of major agronomic traits are important in hybrid combination for the various Corn Belt regions, and have an impact on hybrid performance.

Inbred line development and hybrid testing have been emphasized in the past half-century in commercial maize production as a means to increase hybrid performance. Inbred development is usually done by pedigree selection. Pedigree selection can be selection in an $F_2$ population produced from a planned cross of two genotypes (often elite inbred lines), or selection of progeny of synthetic varieties, open pollinated, composite, or backcross populations. This type of selection is effective for highly inheritable traits, but other traits, for example, yield requires replicated test crosses at a variety of stages for accurate selection.

Maize breeders select for a variety of traits in inbred that impact hybrid performance along with selecting for acceptable parental traits. Such traits include yield potential in hybrid combination; dry down; maturity; grain moisture at harvest; greensnap; resistance to root lodging; resistance to stalk lodging; grain quality; disease and insect resistance; ear and plant height; performance in different soil types such as: low levels of organic matter, clay, sand, black, high pH, low pH; performance in: wet environments, drought environments, and no tillage conditions. These traits appear to be governed by a complex genetic system that makes selection for breeding of an inbred line extremely difficult. Even if an inbred in hybrid combination has excellent yield (a desired characteristic), it may not be useful because it fails to have acceptable parental traits such as seed yield, seed size, pollen production, good silks, plant height, etc.

To illustrate the difficulty of breeding and developing inbred lines, the following example is given. Tow inbreds compared for similarity of 29 traits differed significantly for 18 traits between the two lines. If 18 simply inherited single gene traits were polymorphic with gene frequencies of 0.5 in the parental lines, and assuming independent segregation (as would essentially be the case if each trait resided on a different chromosome arm), then the specific combination of these traits as embodied in an inbred would only be expected to become fixed at a rate of one in 262,144 possible homozygous genetic combinations. Selection of the specific inbred combination is also influenced by the specific selection environment on many of these 18 traits which makes the probability of obtaining this one inbred even more remote. In addition, most traits in the corn genome are regrettably not single dominant genes but are multi-genetic with additive gene action not dominant gene action. Thus, the general procedure of producing a non segregating $F_1$ generation and self pollinating to produce a $F_2$ generation that segregates for traits and selecting progeny with the visual traits desired does not easily lead to a useful inbred. Great care and breeder expertise must be used in selection of breeding material to continue to increase yield and agronomics of inbreds and resultant commercial hybrids. Certain regions of the cornbelt have specific difficulties that other regions may not have. Thus the hybrids developed from the inbreds must to have traits that overcome or at least minimize these regional growing problems. Examples of these problems include: in the easter cornbelt, Gray Leaf Spot; in the north, cool temperatures during seeding emergence; in the Nebraska region, CLN (corn Lethal necrosis; and, in the western region, soil that has excessively high pH levels. The industry often targets inbreds that address these issues specifically to the areas that they occur forming niche products. However the aim, of most large seed producers, is to provide a number of traits to each inbred so that the corresponding hybrid can useful in a broader regions of the cornbelt. The new biotechnology techniques such as microsatellites, RFLPs, RAPDs, and the like have provided breeders with additional tools to accomplish these goals.

SUMMARY OF THE INVENTION

The present invention relates to an inbred corn line ZS4199. Specifically, this invention relates to plants and seeds of this line. Additionally, this invention relates to a method of producing hybrid seed corn from the inbred. More particularly, this invention relates to the unique combination of traits that combine in the corn line ZS4199.

Generally then, broadly the present invention includes an inbred corn seed designated ZS4199. This seed produces a corn plant.

The invention also includes the tissue culture of regenerable cells of ZS4199 wherein the tissue regenerates plants having the phenotype of ZS4199. The tissue culture is selected from the group consisting of leaves, pollen, embryos, roots, root tips, anthers, silk, flowers, kernels, ears, cobs, husks and stalks, and cells and protoplasts thereof. The corn plant regenerated from ZS4199. This includes regenerated corn plants that have ZS4199's genotype or mutants, trangenics or variants thereof.

The invention extends to hybrid seed produced by planting, in pollinating proximity or by using preserved maize pollen as explained in U.S. Pat. No. 5,596,838 to Greaves, seeds of corn inbred lines ZS4199 and another inbred line if pollen is not used; cultivating corn plants resulting from said planting; preventing pollen production by the plants of one of the inbred lines; having cross pollination occur between said inbred lines; and harvesting seeds produced on plants of the inbred. Cross pollination may occur by wind, mechanically or by hand pollination. The invention extends to hybrid seed produced by hybrid combination of plants of inbred corn seed designated ZS4199 and plants of another inbred line. Additionally, the invention extends to hybrid plants and the plant parts including the grain and pollen grown from this hybrid seed.

The invention further includes two methods of hybrid F1 production. In one the present invention is employed for production of seed in the other method for its production of pollen. A first generation (F1) hybrid corn plant produced by the process of planting, seeds of corn inbred line ZS4199; cultivating corn plants resulting from said planting; permitting pollen from another inbred line to cross pollinate inbred line ZS4199; harvesting seeds produced on plants of the inbred ZS4199; and growing a harvested seed.

A first generation (F1) hybrid corn plant produced by the process of planting, seeds of corn inbred line ZS4199; cultivating corn plants resulting from said planting; permitting pollen from inbred line ZS4199 to cross pollinate another inbred line; harvesting seeds produced on plants of the inbred; and growing a harvested seed.

The present invention encompasses the inbred corn line ZS4199 and at least herbicide resistance or disease resistance or other altered traits. In a specific embodiment the inbred corn line ZS4199 contains at least one transgenic gene adapted to give ZS4199 modified starch or oil trains, and/or least one mutant gene adapted to give modified starch or oil traits. In another embodiment of the present invention the inbred corn line ZS4199 contains at least one transgenic gene selected from the group consisting of: bacillus thuringiensis, the bar gene which provides resistance to flugosinate as does the GDHa gene, and the pat gene (encoding phosphinothricin acetyl transferase). Additional herbicide resistant genes includes the 5-enolpyruvylshikimate-3-phosphate (EPSP) synthase gene which provide the plant with resistance to glyphosate. The present invention may also carry trait altering genes such as a low phytic acid producing gene. Additionally, the inbred corn line ZS4199 may contain at least one transgenic gene useful as a selectable marker or a screenable marker.

The scope of the invention includes a tissue culture of the regenerable cells of hybrid plant produced with the use of ZS4199 genetic material. And tissue culture of the regenerable cells of the corn plant produced by the method described above. Furthermore, the scope of the present invention includes production of new lines by haploid induction followed by dihaploid induction of F1 seeds and their plants of the present invention.

DEFINITIONS

In the description and examples that follow, a number of terms are used. In order to provide a clear and consistent understanding of the specifications and claims, including the scope to be given such terms, the following definitions are provided.

BL Moist

The moisture percentage of the grain at black layer, i.e., when 50% of the plants per plot have reached physiological maturity.

Cold Germ

Cold Germ is a measurement of seed germination under cold soil conditions. Data is reported at percent of seed germinating.

ECB

European corn borer a maize eating insect. ECBI is the first brood generation of European corn borers. ECBII is the second generation of European corn borers.

Emerge

The number of emerged plants per plot (planted at the same seedling rate) collected when plants have two fully developed leaves.

GI

This is a selection index that provides a single quantitative measure of the worth of a hybrid based on four traits. Yield is the primary trait contributing to index values. The GI value is calculated by combining stalk lodging, root lodging, yield and dropped ears according to the attached mathematical formula:

$$GI=100+0.5(YLD)-0.9(\%STALK\ LODGE)-0.9(\%ROOT\ LODGE)-2.7(\%DROPPED\ EAR)$$

GLS

Gray Leaf Spot (*Cercospora Zeae*) disease rating. This rated on a 1–9 scale with a "1" being very susceptible, and a "9" being very resistant.*

GW

Goss' Wilt (*Corynebacterium nebraskense*). This rated on a 1–9 scale with a "1" being very susceptible, and a "9" being very resistant.*

HEATP10

The number of Growing Degree Units (GDU's) or heat units required for an inbred line or hybrid to have approximately 10 percent of the plants shedding pollen. This trait is measured from the time of planting. Growing Degree Units are calculated by the Barger Method where the GDU's for a 24 hour period are:

$$GDU = \left(\frac{\text{Max Temp (° F.)} + \text{Min Temp (° F.)}}{2}\right) - 50$$

The highest maximum temperature used is 86° F. and the lowest minimum temperature used is 50° F. For each inbred or hybrid it takes a certain number of GDU's to reach various stages of plant development.

HEATBL

The number of GDU's after planting when approximately 50 percent of the inbred or hybrid plants in a plot have grain that has reached physiological maturity (black layer).

Heatpeek

The number of GDU's after planting of an inbred when approximately 50 percent of the plants whose visible tassel extension.

HEATP50 or HTP50

The number of GDU's required for an inbred or hybrid to have approximately 50 percent of the plants shedding pollen. Growing Degree Units are calculated by the Barger Method as shown in the HEATP10 definition.

HEATP90

The number of GDU's accumulated from planting when the last 100 percent of plants in an inbred or hybrid are still shedding enough viable pollen for pollination to occur. Growing Degree Units are calculated by the Barger Method as shown in the HEATP10 definition.

HEATS10

The number of GDU's required for an inbred or hybrid to have approximately 10 percent of the plants with silk emergence of at least 0.5 inches. Growing Degree Units are calculated by the Barger Method as shown in the HEATP10 definition.

HEATS50 or HTS50

The number of GDU's required for an inbred or hybrid to have approximately 50 percent of the plants with silk emergence of at least 50 inches. Growing Degree Units are calculated by the Barger Method as shown in the HEATP10 definition.

HEATS90

The number of GDU's required for an inbred or hybrid to have approximately 90 percent of the plants with silk emergence of at least 50 inches. Growing Degree Units are calculated by the Barger Method as shown in the HEATP10 definition.

$MDMV_A$

Maize Dwarf Mosaic Virus strain A. The corn is rated on a 1–9 scale with a "1" being very susceptible, and a "9" being very resistant.*

$MDMV_B$

Maize Dwarf Mosaic Virus strain B. This is rated on a 1–9 scale with a "1" being very susceptible and a "9" being very resistant.*

Moisture

The average percentage grain moisture of an inbred or hybrid at harvest time.

NLB

Northern Leaf Blight (*Exserohilum turcicum*) disease rating. This is rated on a 1–9 scale with "1" being very susceptible, and a "9" being very resistant.*

PCT Tiller

The total number of tillers per plot divided by the total number of plants per plot.

Plant

This term includes plant cells, plant protoplasts, plant cell tissue cultures from which corn plants can be regenerated, plant cells, plant clumps, and plant cells that are intact in plants or parts of plants, such as embryos, pollen, flowers, kernels, ears, cobs, leaves, husks, stalks, roots, root tips, anthers, silk and the like, and this term also includes any transgenic DNA or (RNA) or portion thereof that have been introduced into the plant by whatever method.

Plant Height

The distance in centimeters from ground level to the base of the tassel peduncle.

RM

Predicted relative maturity based on the moisture percentage of the grain at harvest. This rating is based on known set of checks and utilizes standard linear regression analyses and is referred to as the Minnesota Relative Maturity Rating System.

Shed

The volume of pollen shed by the male flower rated on a 1–9 scale where "1" is a very light pollen shredder, a "4.5" is a moderate shredder, and a "9" is a very heavy shedder.

SLB

Southern Leaf Blight (*Bipolaris maydis*) disease rating. This is rated on a 1–9 scale with a "1" being very susceptible, and a "9" being very resistant.*

TWT

The measure of a weight of grain in pounds for a one bushel volume adjusted for percent grain moisture.

Vigor

Visual rating of 1 to 9 made 2–3 weeks post-emergence where a "1" indicates very poor early plant development, and a "9" indicates superior plant development.

Warm Germ

A measurement of seed germination under ideal (warm, moist) conditions. Data is reported as percent of seeds germinating.

Yield (YLD)

Actual yield of grain at harvest adjusted to 15.5% moisture. Measurements are reported in bushels per acre.

% Dropped Ears (DE)

The number of plants per plot which dropped their primary ear divided by the total number of plants per plot.

% LRG Flat

Percentage by weight of shelled corn that passes through a 26/64 inch round screen and a 14/64 inch slot screen, but does not pass through a screen with 20.5/64 inch round openings.

% LRG Round

Percentage by weight of shelled corn that passes through a 26/64 inch round screen, but does not pass through a 14/64 inch slot screen or a screen with 20.5/64 inch round openings.

% MED Flat

Percentage by weight of shelled corn that passes through a 20.5/64 inch round screen and a 13/64 inch slotted screen, but does not pass through a screen with 17/64 inch round openings.

% MED Round

Percentage by weight of shelled corn that passes through a 20.5/64 inch round screen, but does not pass through a 13/64 inch slot screen or a screen with 17/64 inch round openings.

% SML Flat

Percentage by weight of shelled corn that passes through a 17/64 inch round screen and a 12/64 inch slotted screen, but does not pass through a screen with 15/64 inch round openings.

% SML Round

Percentage by weight of shelled corn that passes through a 17/64 inch round screen, but does not pass through a 12/64 inch slotted screen or a screen with 15/64 inch round openings.

% Root Lodge (RL)

Percentage of plants per plot leaning more that 30 degrees from vertical divided by total plants per plot.

% Stalk Lodge (SL)

Percentage of plants per plot with the stalk broken below the primary ear node divided by the total plants per plot.
*Resistant—on a scale of 1–9 with 9 evidencing the trait most strongly: 1–2.9 ratings are susceptible, 3–5.9 ratings are intermediate, and 6–9 ratings are resistant.

DETAILED DESCRIPTION OF THE INVENTION

ZS4199 can be used as a male line or a female line but is preferred as a male. This ZS4199 line shows good yielding potential, good pollen shed and excellent female seed yields in the inbred.

This inbred shows medium to high levels of disease and borer resistance, excellent, vigor and emergence and warm germination quality. When in hybrid combination, this inbred frequently carries consistent levels of high yield potential into the hybrid cross environments.

The inbred has shown uniformity and stability within the limits of environmental influence for all the traits as described in the Variety Description Information (Table 1) that follows.

The inbred has been self-pollinated for a sufficient number of generations to give inbred uniformity. During plant selection in each generation, the uniformity of plant type was selected to ensure homozygosity and phenotypic stability. The line has been increased in isolated farmland environments with data on uniformity and agronomic traits being observed to assure uniformity and stability. No variant traits have been observed or are expected in ZS4199.

The best method of producing the invention, ZS4199 which is substantially homozygous, is by planting the seed of ZS4199 which is substantially homozygous and self-pollinating or sib pollinating the resultant plant in an isolated environment, and harvesting the resultant seed.

TABLE 1

ZS4199
VARIETY DESCRIPTION INFORMATION
1 Type: Dent - 103 RM in hybrid combination
2 Region Best Adapted: Broadly adapted - cross the combelt,
PVP TRAITS
INBRED ZS4199

|  | N | MEAN | STD. | 95% CI |
|---|---|---|---|---|
| EAR HEIGHT (CM) |  | 58.67 | 8.72 | (54.25, 63.08) |
| LENGTH OF PRIMARY EAR LEAF (CM) | 15 | 87.67 | 3.44 | (85.93, 89.41) |
| WIDTH OF PRIMARY EAR LEAF (CM) | 15 | 10.12 | 0.65 | (9.79, 10.45) |
| TOP EAR INTERNODE (CM) | 15 | 14.19 | 1.66 | (13.35, 15.03) |
| DEGREE OF LEAF ANGLE | 15 | 31.33 | 4.32 | (29.15, 33.52) |
| # OF EARS PER PLANT | 15 | 1.47 | 0.52 | (1.21, 1.73) |
| # OF LEAVES ABOVE TOP EAR | 15 | 5.47 | 0.52 | (5.21, 5.73) |
| # OF PRIMARY LATERAL TASSEL BRANCHES | 15 | 3.93 | 1.53 | (3.16, 4.71) |
| PLANT HEIGHT (CM) | 15 | 202.5 | 10.84 | (197.0, 208.0) |
| TASSEL LENGTH (CM) | 15 | 42.80 | 2.96 | (41.30, 44.30) |
| TASSEL BRANCH ANGLE | 15 | 16.67 | 6.86 | (13.19, 20.14) |
| # OF TILLER PER PLANTS | 15 | 0.00 | 0.00 | (0.00, 0.00) |
| WEIGHT PER 100 KERNELS (GM) | 15 | 24.01 | 2.44 | (22.78, 25.25) |
| EAR LENGTH (CM) | 15 | 19.29 | 1.23 | (18.67, 19.92) |
| EAR WEIGHT (GM) | 15 | 127.6 | 14.89 | (120.1, 135.2) |
| # OF KERNEL ROWS | 15 | 13.33 | 0.98 | (12.84, 13.83) |
| COB DIAMETER AT MID-POINT (MM) | 15 | 22.28 | 0.83 | (21.86, 22.70 |
| EAR DIAMETER AT MID-POINT (MM) | 15 | 37.70 | 1.35 | (37.02, 38.38) |
| KERNEL LENGTH (MM) | 15 | 10.75 | 0.69 | (10.40, 11.10) |
| KERNEL THICKNESS (MM) | 15 | 5.11 | 0.75 | (4.73, 5.49) |
| KERNEL WIDTH (MM) | 15 | 7.87 | 0.61 | (7.56, 8.17) |
| % ROUND KERNELS (SHAPE GRADE) | 15 | 30.01 | 9.84 | (25.03, 34.99) |
| SHANK LENGTH | 15 | 7.96 | 1.94 | (6.98, 8.94) |

INBRED ZS4199

| #3 | MATURITY | | |
|---|---|---|---|
| DAYS | HEAT UNITS | | |
| 74 | 1492 | | FROM PLANTING TO 50% OF PLANTS IN SILK |
| 74 | 1492 | | FROM PLANTING TO 50% OF PLANTS IN POLLEN |
| 2 | | | FROM 10% TO 90% POLLEN SHED |
| #4 | PLANT DATA | | |
| 1 | | | ANTHOCYANIN OF BRACE ROOTS: 1 = ABSENT  2 = FAINT  3 = MODERATE  4= DARK |

TABLE 1-continued

5 LEAF

COLOR/DATA

| | |
|---|---|
| 3/DARK GREEN | LEAF COLOR **MUNSELL CODE - 5GY 4/4 |
| 6 | LEAF SHEATH PUBESCENCE (1 = NONE TO 9 = PEACH FUZZ) |
| 4 | MARGINAL WAVES (1 = NONE TO 9 = MANY) |
| 7 | LONGITUDINAL CREASES (1 = NONE TO 9 = MANY) |

6 TASSEL

COLOR/DATA

| | |
|---|---|
| 7 | POLLEN SHED (0 = STERILE TO 9 = HEAVY SHEDDER) |
| 5/GREEN-YELLOW | ANTHER COLOR **MUNSELL CODE - 2.5HY 8/6 |
| 2 & 17/MGRN/PUR | GLUME COLOR **MUNSELL CODE - 5GY 5/6 W/5R 5/6 |
| 1 | BAR GLUME: 1 = ABSENT  2 = PRESENT |

7A EAR (UNHUSKED DATA)

COLOR/DATA

| | |
|---|---|
| 5/GREEN-YELLOW | SILK COLOR (3 DAYS AFTER EMERGE) **MUNSELL CODE - 2.5GY 8/6 |
| 1/LIGHT GREEN | FRESH HUSK (25 DAYS AFTER 50% SILK) **MUNSELL CODE - 2.5GY 7/6 |
| 6/PALE YELLOW | DRY HUSK COLOR (65 DAYS AFTER 50% SILK **MUNSELL CODE - 5Y 8/4 |
| 1 | POSITION OF EAR AT DRY HUSK: 1 = UPRIGHT  2 = HORIZONTAL  3 = PENDENT |
| 4 | HUSK TIGHTNESS (1 = VERY LOOSE TO 9 = VERY TIGHT) |
| 3 | HUSK EXTENSION AT HARVEST: 1 = EXPOSED EAR  2 = 8 CM  3 = 8–10 CM  4 = >10 CM |

7B EAR (HUSKED DATA)

DATA

| | |
|---|---|
| 2 | KERNEL ROSE: 1 = INDISTINCT  2 = DISTINCT |
| 1 | ROW ALIGNMENT: 1 = STRAIT  2 = SLIGHT CURVE  3 = SPIRAL |
| 2 | EAR TAPPER: 1 = SLIGHT  2 = AVERAGE  3 = EXTREME |

TABLE 1-continued

8 KERNEL (DRY)

COLOR/DATA

| | |
|---|---|
| 1 | ALEURONE COLOR PATTERN: 1 = HOMO  2 = SEG |
| 8/YELLOW-ORNGE | ALEURONE COLOR **MUNSELL CODE - 7.5YR 7/10 |
| 8/YELLOW-ORNGE | HARD ENDOSPERM COLOR **MUNSELL CODE - 7.5YR 6/10 |
| 3 | ENDOSPERM TYPE |
| 7/YELLOW | CROWN COLOR **MUNSELL CODE - 2.5Y 8/10 |

9 COB

COLOR

| | |
|---|---|
| 21/BUFF | COB COLOR **MUNSELL CODE-2.5Y 8/4 |

COLOR CHOICES (Use in conjunction with Munsell color code to describe all color choices; describe #25 and #26 in Comments section):

| | |
|---|---|
| 01 = Light Green | 14 = Red |
| 02 = Medium Green | 15 = Red & White |
| 03 = Dark Green | 16 = Pale Purple |
| 04 = Very Dark Green | 17 = Purple |
| 05 = Green-Yellow | 18 = Colorless |
| 06 = Pale Yellow | 19 = White |
| 07 = Yellow | 20 = White Capped |
| 08 = Yellow-Orange | 21 = Buff |
| 09 = Salmon | 22 = Tan |
| 10 = Pink-Orange | 23 = Brown |
| 11 = Pink | 24 = Bronze |
| 12 = Light Red | 25 = Variegated (Describe) |
| 13 = Cherry Red | 26 = Other (Describe) |

The Munsell code referred to above is a reference book of color which is known and used in the industry and by persons with ordinary skill in the art of plant breeding.

The purity and homozygosity of inbred ZS4199 is constantly being tracked using isozyme genotypes as shown in Table 2.

Isozyme Genotypes for ZS4199

Isozyme data were generated for inbred corn line ZS4199 according to procedures known and published in the art. The data in Table 2 gives the electrophoresis data on ZS4199 as compared to its two parents.

TABLE 2

ELECTROPHORESIS RESULTS FOR ZS4199

| INBRED | ACP1 | ACP4 | ADH | MDH1 | MDH2 | PGD1 | PGD2 | PH1 | PGM | IDH |
|---|---|---|---|---|---|---|---|---|---|---|
| ZS4199 | 33 | 0 | 22 | 22 | 22 | 11 | 11 | 22 | 22 | 22 |

Inbred and Hybrid Performance of ZS4199

The traits and characteristics of inbred corn line ZS4199 are listed in comparison to other inbreds and/or hybrids. The ZS4199 data shows the characteristics and traits of importance, giving a snapshot of ZS4199 in these specific environments.

Table 3A shows a comparison between ZS4199 and the comparable inbred ZS01131. ZS4199 has significantly more seedling vigor than does inbred ZS01131. ZS4199 has significantly more yield at harvest, than does ZS01131. ZA4199 flowers similarly to ZS01131 across all pollination and silking data, except HEATS50 where ZS4199 is significantly earlier. ZS4199 has significantly later HEATPEEK than does ZS01131. ZS4199 has significantly better cold germination results and significantly more medium round seeds than does ZS01131.

Table 4 shows ZS4199 in XR crossed to different inbreds to form various hybrid combinations. ZS4199 in hybrid combination shows an advantage for resisting root lodging and an equal position with the checks concerning stalk lodging, and dropped ears. Additionally, ZS4199 in hybrid combination shows an advantage for yield over moisture and for moisture. Although not shown above the advantage for moisture and for root lodging increases if the data only shows those parents with two years of data.

TABLE 3A

| YEAR | INBRED | VIGOR | EMERGE | PCT TILLER | PLANT HEIGHT | EAR HEIGHT | SHED | EAR QUALITY | PCT BARREN | HEATP10 | HEATP50 |
|---|---|---|---|---|---|---|---|---|---|---|---|
| OVERALL | ZS4199 | 7.1 | 86.6 | | 161.7 | 66.4 | 6.5 | | | 1458 | 1506 |
| | ZS01131 | 5.3 | 76.7 | | 178.2 | 73.5 | 6.4 | | | 1466 | 1510 |
| | # EXPTS | 17 | .16 | | 17 | 17 | 11 | | | 13 | 13 |
| | DIFF | 1.8 | 9.9 | | 16.5 | 7.1 | 0.2 | | | 7 | 3 |
| | PROB | 0.000*** | 0.000*** | | 0.000*** | 0.005*** | 0.553 | | | 0.474 | 0.742 |

| YEAR | INBRED | HEATP90 | HEATS10 | HEATS50 | HEATS90 | HEATPEEK | HEATBL | BL MOIST | % ROOT LODGE | % STALK LODGE | % DROPPED EARS |
|---|---|---|---|---|---|---|---|---|---|---|---|
| OVERALL | ZS4199 | 1594 | 1470 | 1506 | 1549 | 1389 | 2459 | | | | |
| | ZS01131 | 1617 | 1490 | 1534 | 1570 | 1364 | 2577 | | | | |
| | # EXPTS | 10 | 13 | 13 | 13 | 13 | 1 | | | | |
| | DIFF | 23 | 20 | 28 | 21 | 25 | 118 | | | | |
| | PROB | 0.234 | 0.126 | 0.049** | 0.159 | 0.008*** | | | | | |

| YEAR | INBRED | MOISTURE | YIELD | WARM GERM | COLD GERM | % LRG ROUND | % LRG FLAT | % MED ROUND | % MED FLAT | % SML ROUND | % SML FLAT |
|---|---|---|---|---|---|---|---|---|---|---|---|
| OVERALL | ZS4199 | 11.7 | 95.7 | 95.5 | 83.2 | | | 30.6 | 31.0 | | |
| | ZS01131 | 11.6 | 72.1 | 92.1 | 88.4 | | | 23.0 | 33.6 | | |
| | # EXPTS | 18 | 18 | 10 | 9 | | | 17 | 17 | | |
| | DIFF | 0.1 | 23.6 | 3.4 | 5.2 | | | 7.6 | 2.6 | | |
| | PROB | 0.707 | 0.000*** | 0.012** | 0.313 | | | 0.001*** | 0.245 | | |

*.05 < PROB <= .10
**.01 < PROB <= .05
***.00 < PROB <= .01

Table 4 shows the GCA (general combining ability) estimates of ZS4199 compared with the GCA estimates of the other inbreds. The estimates show the general combining ability is weighted by the number of experiment/location combinations in which the specific hybrid combination occurs. The interpretation of the data for all traits is that a positive comparison is a practical advantage. A negative comparison is a practical disadvantage. The general combining ability of an inbred is clearly evidenced by the results of the general combining ability estimates. This data compares the inbred parent in a number of hybrid combinations to a group of "checks". The check data is from other companies' hybrids. Particularly the leader in the industry and Garst Seed Company's commercial products and pre-commercial hybrids which were grown in the same sets and locations.

TABLE 5A

| YIELD RESPONSE | | | | | | |
|---|---|---|---|---|---|---|
| Research Plots HYBRID | | | YIELD | | | |
| ZS4199/Inbred | 86 | 110 | 134 | 158 | 183 | 207 |
| Environment | 75 | 100 | 125 | 150 | 175 | 200 |
| Error: 14.4 | | | | | | |
| # Plots 369 | | | | | | |

TABLE 4

ZS4199

| N | FI | Y/M | GI | YLD | MST | % SL | % RL | % DE | TWT | POP | RM |
|---|---|---|---|---|---|---|---|---|---|---|---|
| XR = 5117 | 1.1 | 0.2 | −0.2 | −1.6 | 0.6 | 0.0 | 0.5 | 0.0 | −0.1 | 34 | 108 |

XR = General combining ability estimate weighted by experiment

TABLE 5B

YIELD RESPONSE

Research Plots
HYBRID                              YIELD

ZS4199/Inbred      72    99   125   151   177   204
Environment        75   100   125   150   175   200
Error 15.9
Strips 167

Table 5A & B shows the yield response of ZS4199 in hybrid combination in comparison with the plants in the environment around it at the same location. Plots are smaller areas than are strips. In this instance, the data is slightly different. However, it appears that the inbred in hybrid combination in the strip data is equal to or out yielding the checks in across all the environments. ZS4199 in hybrid combination in the plots yields better than the environment in all yielding environments. The yield in both sets is about equal to or slightly better than the yield of the environments. Its performance shows that this is an inbred that can provide outstanding results regardless of the quality of the environment.

TABLE 6

HYBRID SUMMARY
PERFORMANCE DATA

| HYBRID | N | FI | Y/M | YLD | MST | % SL | % RL | % DE | TWT |
|---|---|---|---|---|---|---|---|---|---|
| CT/ZS4199 8541IT | 245 | 2.9 | +0.6 | +0.6 | +1.3 | +0.0 | +0.1 | +0.1 | +1.1 |

CT = common tester. This is a common tester that is in hybrid 8541IT.

ZS4199 has an advantage in many categories over the other commercial hybrid 8541IT. The above data indicates the positive or negative difference between the present invention and the listed hybrid. There is a large positive difference in yield, moisture, yield over moisture and in testweight for the present invention when in hybrid combination. In fact, the present invention has advantage over all of the traits.

HYBRID SUMMARY
ZS4199/INBRED
AGRONOMIC DATA ACROSS THREE YEARS

| HYBRID | N | EMG | VIG | SGN | INT |
|---|---|---|---|---|---|
| CT/ZS4199 8541IT | 49 | +0.3 | +0.5 | −1 | +0.1 |

ZS4199 when in this hybrid combination has an advantage or is equal in all categories over the other commercial hybrid 8541IT except for staygreen. The above data indicates the positive or negative difference between the present invention and the listed hybrid.

TABLE 6b

HYBRID SUMMARY
PERFORMANCE DATA

| HYBRID | N | FI | Y/M | YLD | MST | % SL | % RL | % DE | TWT |
|---|---|---|---|---|---|---|---|---|---|
| CT/ZS4199 8640 | 212 | 2.8 | −0.5 | +5.5 | −1.4 | +1.3 | +1.8 | +0.2 | +0.8 |

CT=common tester. This is a common tester that is in hybrid 8640. ZS4199 has an advantage in many categories over the other commercial hybrid 8640. The above data indicates the positive or negative difference between the present invention and the listed hybrid. There is a large significant positive difference in yield and in testweight. There is unfortunately a negative difference in moisture, and yield over moisture for the present invention when in hybrid combination. In fact, the present invention has advantage over all of the traits of root and stalk lodging.

HYBRID SUMMARY
ZS4199/INBRED
AGRONOMIC DATA ACROSS THREE YEARS

| HYBRID | N | EMG | VIG | SGN | INT |
|---|---|---|---|---|---|
| CT/ZS4199 8640 | 59 | −0.3 | −0.2 | 0.0 | +0.5 |

ZS4199 when in this hybrid combination has an advantage or is equal in staygreen and integrity categories over the other commercial hybrid 8640. The above data indicates the positive or negative difference between the present invention and the listed hybrid.

This invention also is directed to methods for producing a corn plant by crossing a first parent corn plant with a second corn plant wherein the first or second parent corn plant is an inbred corn plant from the line ZS4199. Further, both first and second parent corn plants can come from the inbred corn line ZS4199. A variety of breeding methods can be selected depending on the mode of reproduction, the trait, the condition of the germplasm. Thus, any such methods using the inbred corn line ZS4199 are part of this invention: selfing, backcrosses, hybrid production, induction of apomixis, crosses to populations, haploid by such old and known methods of using stock 6 material that induces haploids and anther culturing and the like.

Additionally, this plant can, within the scope of the invention, contain: a mutant gene such as but not limited to sugary 1, shrunken 1, waxy, AE, low phytic acid mutation (patented by Raboy of USDA) or imazethapyr tolerant (IT or IR™) mutant genes. The present invention can also comprise transgenic genes such as, but not limited to insect resistant genes such as *Bacillus thuringiensis* (Cry genes), or herbicide resistant genes such as Pat gene, GDHa, glutamate dehydrogenase, or Bar gene (these three genes provide resistance to glufosinate), EPSP (provides resistance to glyphosate), IMI genes (provides imagethapyr resistance), or disease resistant genes such as coat protein genes, genes which encode a Mosaic virus resistance, and genes which encode Gray leafspot resistance for trait altering genes such as fructosyl transferase encoding genes, trehalose encoding genes, polysaccharide modifying genes, senescence controlling genes, male sterility genes, etc.

Included within the scope of the invention is a host of conventional and unconventional methods of manipulating corn genetics such as various culturing techniques known to those skilled in the art, haploid and dihaploid induction, transposon tagging, transformation and using preserved pollen for breeding. Regardless of the techniques employed, all plants and plant cells produced using the inbred corn plant or its progeny are within the scope of this invention.

The term transgenic plant refers to a plant having at least one genetic sequence introduced into the genome of the plant by a transformation method and the progeny of said plant. A transgenic plant can be formed by a number of transformation methods. These methods are means for integrating new genetic coding sequences into the plant's genome. The basic steps of transforming monocots are shown in the art. These type of transforming steps are concisely outlined in U.S. Pat. No. 5,484,956 "Fertile Transgenic Zea mays Plants Comprising heterologous DNA Encoding Bacillus Thuringiensis Endotoxin" issued Jan. 16, 1996 and in U.S. Pat. No. 5,489,520 "Process of Producing Fertile Zea mays Plants and Progeny Comprising a Gene Encoding Phosphinothricin Acetyl Transferase" issued Feb. 6, 1996.

Plant cells such as maize can be transformed in other ways also. A number of different transformation techniques have been successful. Some of these techniques which have been reported on and are known in the art, these include maize pollen transformation (See University of Toledo 1993 U.S. Pat. No. 5,177,010); Biolistic gun technology (See U.S. Pat. No. 5,484,956); Whiskers technology (See U.S. Pat. Nos. 5,464,765 and 5,302,523); Electroporation; PEG on Maize protoplasts; Agrobacterium (See 1996 article on transformation of maize cells in Nature Biotechnology, Volume 14, June 1996). There are numerous other transformation methods which may have slightly lower efficiency rates then those listed.

Some of these transformation methods require specific types of tissue or cells and other methods can be practiced on any number of cell types. The use of pollen, cotyledons, meristems, zygotes and ovum as the target tissue can eliminate the need for extensive tissue culture work. Generally, cells derived from meristematic tissue are useful. Zygotic embryos can also be used. The method of transformation of meristematic cells of cereals in general is also taught in the PCT application WO96/04392.

Many of the various cell lines, tissues, plant parts can and have been transformed by those having knowledge in the art. Methods of preparing callus from various plants are well known in the art and specific methods are detailed in patents and references used by those skilled in the art. Cultures can be initiated from most of the above identified tissue. The only true requirement is that the material used for transforming can be developed into a transformed plant.

The genetic material used in the transformation process can come from almost any living source such as bacteria, yeast, animals, viruses, algae or plants. This DNA used in the transformation process may be circular, linear, double or single stranded. Usually, the DNA is in the form of a plasmid. The methods of forming plasmids for transformation are known in the art. The plasmid most often contains regulatory and/or targeting sequences which assists the expression of the gene in the plant. Plasmid components can include such items as: leader sequences, transit polypeptides, promoters, terminators, genes, introns, marker genes, etc. The structure of the gene's orientation within the plasmid components can be sense, antisense, partial antisense, or partial sense. Gene as used here in includes natural, synthetic, DNA and RNA sequences of any length beyond 1 base pair.

The regulatory promoters employed can be constitutive such as CaMv35S (usually for dicots) and polyubiquitin for mmonocots or tissue specific promoters such as CAB promoters, etc. The prior art includes a number of promoters to select from such as rice actin promoters, octopine synthase, nopaline synthase, CaMv19S, mannopine synthase. These regulatory sequences can be combined with introns, terminators, enhancers, leader sequences and the like in the material used for transformation.

After the transformation of the plant material is complete, the next step is identifying the cells or material which are transformed. Presently, PCR is often employed to identify transformants. In some cases, a screenable marker is employed such as the beta-glucuronidase gene of the uidA locus of E. coli. Then, the transformed cells expressing the colored protein are selected for either regeneration or further use. In many cases, the transformed material is identified by a selectable marker. The putatively transformed material is exposed to a toxic agent at varying concentrations. The cells which are not transformed with the selectable marker die. Cells or tissues containing the resistant selectable marker generally proliferate. It has been noted that although selectable markers protect the cells from some of the toxic affects of the herbicide or antibiotic, the cells may still be slightly effected by the toxic agent by having slower growth rates. The transformed material selected by this process are regenerated into plants. The cell's lines are treated to induce tissue differentiation. Methods of regeneration of cellular maize material are well known in the art. The plants derived directly from either the transformation process or the regeneration process or crossed to either such plants or a progeny of such plants are transgenic plants.

All plant and plant cells produced using inbred corn line ZS4199 are within the scope of this invention. The invention encompasses the inbred corn line used in crosses with other, different, corn inbreds to produce (F1) corn hybrid seeds and plants with the characteristics that make desirable hybrids. This invention also includes cells, which upon growth and differentiation produce corn plants having the physiological and morphological characteristics of the inbred line ZS4199.

Additional public information on some ZS designations may be available from the PVP office a division of the US government.

Seeds of this invention will be maintained by Garst Seed Company, 2369 330th Street, Slater, Iowa 50244. Access to this invention will be available during the pendency of this application to the Commissioner of Patents and Trademarks and person determined by the Commissioner to be entitled thereto upon request. All restrictions on availability to the public of such material will be removed upon issuance of a granted patent of this application by depositing at least 2500 seeds of this invention at the American Type Collection, 10801 University Boulevard, Manassas, Va. 20110-2209. The ATCC deposit was tested for viability of the biological material at the time of deposit and found to be viable on Apr. 18, 2000. The accession number is PTA-1468 and the date of deposit of this inbred maize seed was Mar. 22, 2000. The ATCC deposit will be maintained in that depository, which is a public depository, for a period of 30 year, or 5 years after the last request, or for the enforceable life of the patent, whichever is longer, and will be replaced if it becomes nonviable during that period.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

We claim:

1. Inbred corn seed designated ZS4199, some seed of which has been deposited in the ATCC representative samples and designated as accession number PTA-1648.

2. A corn plant produced by the seed of claim 1.

3. A tissue culture of regenerable cells of ZS4199 of claim 2 wherein the cells of the tissue culture regenerate plants capable of expressing the genotype of ZS4199.

4. A tissue culture according to claim 3, the tissue culture selected from the group consisting of leaves, pollen, embryos, roots, root tips, anthers, silk, flowers, kernels, ears, cobs, husks and stalks, and cells and protoplasts thereof.

5. A corn plant capable of expressing the genotype of ZS4199 regenerated from the cells of the tissue culture of claim 3.

6. Hybrid seed produced by:
   (a) planting, in pollinating proximity, seeds of corn inbred lines ZS4199 which has been deposited in the ATCC representative samples and designated as accession number PTA-1648 and another inbred line, one of said inbred lines not releasing pollen;
   (b) cultivating corn plants resulting from said planting;
   (c) allowing cross pollination to occur between said inbred lines; and
   (d) harvesting seeds produced on the non-pollen releasing inbred.

7. Hybrid seed produced by hybrid combination of plants of inbred corn seed designated ZS4199 in claim 1 and plants of another inbred line.

8. Hybrid plants grown from seed of claim 7.

9. A first generation (F1) hybrid corn plant produced by using ZS4199 which has been deposited in the ATCC representative samples and designated as accession number PTA-1648 the process of:
   (a) planting seeds of corn inbred lines ZS4199 and another inbred line;
   (b) cultivating corn plants resulting from said planting;
   (c) preventing pollen production by the plants of one of the inbred lines;
   (d) allowing pollination between said inbred lines;
   (e) harvesting seeds produced on plants of the inbred line of step (c); and
   (f) growing a harvested seed of step (e).

10. A tissue culture of the regenerable cells of the corn plant of claim 8.

11. A tissue culture of the regenerable cells of the corn plant of claim 9.

12. A plant according to claim 2, including in the plant at least one transgenic gene selected from the following group: insect resistant genes, disease resistant genes, herbicide resistant genes, and trait altering genes.

13. A seed according to claim 1, including at least one transgenic gene selected from the following group: insect resistant genes, disease resistant genes, herbicide resistant genes, and trait altering genes.

14. Hybrid seed containing at least one transgenic gene said seed produced by hybrid combination of plants of inbred corn seed designated ZS4199 in claim 13 and plants of another inbred line.

15. A plant according to claim 2, including in the plant at least one mutant gene.

16. A seed according to claim 1, including at least one mutant gene.

17. Hybrid seed containing at least one mutant gene said seed produced by hybrid combination of plants of inbred corn seed designated ZS4199 in claim 16 and plants of another inbred line.

* * * * *